(12) United States Patent
Choi et al.

(10) Patent No.: US 10,521,069 B2
(45) Date of Patent: Dec. 31, 2019

(54) ULTRASONIC APPARATUS AND METHOD FOR CONTROLLING THE SAME

(71) Applicant: SAMSUNG MEDISON CO., LTD., Hongcheon-gun, Gangwon-do (KR)

(72) Inventors: Sung-Jin Choi, Seoul (KR); Bong Koo Seo, Seoul (KR); Dong Kuk Shin, Guri-si (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 413 days.

(21) Appl. No.: 15/191,447

(22) Filed: Jun. 23, 2016

(65) Prior Publication Data

US 2017/0102854 A1    Apr. 13, 2017

(30) Foreign Application Priority Data

Oct. 8, 2015  (KR) .......................... 10-2015-0141870

(51) Int. Cl.
| | |
|---|---|
| *G06F 3/0481* | (2013.01) |
| *A61B 8/00* | (2006.01) |
| *A61B 8/08* | (2006.01) |
| *G06T 7/33* | (2017.01) |

(52) U.S. Cl.
CPC ........ *G06F 3/04812* (2013.01); *A61B 8/4254* (2013.01); *A61B 8/463* (2013.01); *A61B 8/465* (2013.01); *A61B 8/469* (2013.01); *A61B 8/5246* (2013.01); *A61B 8/54* (2013.01);
(Continued)

(58) Field of Classification Search
CPC .............. A61B 90/36; A61B 2090/364; A61B 2090/367; A61B 2090/378; G06T 7/33
See application file for complete search history.

(56) References Cited

U.S. PATENT DOCUMENTS

| | | | |
|---|---|---|---|
| 5,951,571 A * | 9/1999 | Audette ............... | G06K 9/6211 600/407 |
| 7,966,576 B2 * | 6/2011 | Dongelmans ......... | G06F 3/0486 715/822 |
| 9,460,510 B2 * | 10/2016 | Hermosillo Valadez ................... | G06T 7/33 |

(Continued)

*Primary Examiner* — Li P Sun
*Assistant Examiner* — Eric J Yoon
(74) *Attorney, Agent, or Firm* — Morgan, Lewis & Bockius LLP

(57) ABSTRACT

Disclosed is an ultrasound apparatus and method for controlling the same, whereby once a feature point for re-registration is selected on one of registered ultrasound image and external image, a cursor is displayed on the other image at a point corresponding to the selected feature point. The ultrasonic apparatus includes a controller for using a difference in coordinates between a first feature point of an ultrasound image and a second feature point of an external image with respect to a reference coordinate system, to register the ultrasound image and the external image; a display for displaying the registered ultrasound image and external image; and an input unit for receiving a command to select third and fourth feature points for re-registration, wherein the controller is configured to, once the third feature point of one of the ultrasound image and the external image is selected, control the display to display a cursor for selection of the fourth feature point at a position corresponding to the third feature point on the other one of the ultrasound image and the external image by means of the difference.

9 Claims, 13 Drawing Sheets

(52) U.S. Cl.
CPC .... *G06T 7/337* (2017.01); *G06T 2207/10132* (2013.01); *G06T 2207/20101* (2013.01)

(56) References Cited

U.S. PATENT DOCUMENTS

2006/0036162 A1\* 2/2006 Shahidi .................. A61B 5/06
                                                        600/424
2009/0097778 A1   4/2009 Washburn et al.

\* cited by examiner

ULTRASONIC APPARATUS AND METHOD FOR CONTROLLING THE SAME

CROSS-REFERENCE TO RELATED APPLICATION

This application claims priority to and the benefit of Korean Patent Application No. 10-2015-0141870, filed on Oct. 8, 2015, the disclosure of which is incorporated herein by reference in its entirety.

BACKGROUND

1. Field of the Invention

Embodiments of the present disclosure relate to an ultrasonic apparatus and method for controlling the same, which provides an ultrasound image of an object.

2. Discussion of Related Art

An ultrasonic apparatus irradiates ultrasounds from the surface of an object toward a particular region inside the object and uses information of the reflected echo ultrasounds to noninvasively acquire an image of a cross-section of a soft tissue or blood stream.

The ultrasonic apparatus has many advantages in that it is compact and inexpensive, able to display images in real time, and guarantees high safety because there is no radiation exposure, such as exposure to X rays. Accordingly, the ultrasonic diagnostic equipment is widely used for examination of the heart, breast, abdomen, urinary organs, and examination in women clinic.

Recently, active studies on an ultrasonic apparatus for registering an external image of an object acquired by an external imaging apparatus with an ultrasound image of the object and providing the registration result for the user are underway. Such an ultrasound apparatus may register an external image, such as a Computerized Tomography (CT) image, a Magnetic Resonance (MR) image, etc. of an object with an ultrasound image of the object and display the registration result through a display.

SUMMARY OF THE INVENTION

Embodiments of the present disclosure provide an ultrasound apparatus and method for controlling the same, whereby once a feature point for re-registration is selected on one of registered ultrasound image and external image, a cursor is displayed on the other image at a point corresponding to the selected feature point.

In accordance with an aspect of the present disclosure, an ultrasonic apparatus includes a controller for using a difference in coordinates between a first feature point of an ultrasound image and a second feature point of an external image with respect to a reference coordinate system, to register the ultrasound image and the external image; a display for displaying the registered ultrasound image and external image; and an input unit for receiving a command to select third and fourth feature points for re-registration, wherein the controller is configured to, once the third feature point of one of the ultrasound image and the external image is selected, control the display to display a cursor for selection of the fourth feature point at a position corresponding to the third feature point on the other one of the ultrasound image and the external image by means of the difference.

The controller may control the display to display at least one of a first cursor for selection of the third feature point and a second cursor for selection of the fourth feature point.

While the first and second cursors are displayed at the same time, if the first cursor is moved to select the third feature point, the controller may control the display to display the second cursor at a position corresponding to the moved position of the first cursor by means of the difference.

The controller may control the display to display the first cursor in a changed color, once the third feature point is selected.

The controller may control the display to display an area with emphasis, the area including the position of the second cursor determined by the difference, once the third feature point is selected.

In accordance with another aspect of the present disclosure, a method for controlling an ultrasonic apparatus includes using a difference in coordinates between a first feature point of an ultrasound image and a second feature point of an external image with respect to a reference coordinate system, to register the ultrasound image and the external image; displaying the registered ultrasound image and external image; and receiving a re-registration command; and once a third feature point of one of the ultrasound image and the external image is selected for re-registration, displaying a cursor for selection of a fourth feature point at a position corresponding to the third feature point on the other one of the ultrasound image and the external image by means of the difference.

Displaying a cursor for selection of a fourth feature point may include displaying a first cursor for selection of the third feature point; receiving a command to select the position of the first cursor to be the third feature point; and displaying a second cursor for selection of the fourth feature point at a position corresponding to the third feature point by means of the difference.

The method may further include, once the first cursor is moved to select the third feature point, displaying the second cursor on a position corresponding to a moved position of the first cursor by means of the difference.

The method may further include displaying the first cursor in a changed color, once the third feature point is selected.

The method may further include displaying an area with emphasis, the area including the position of the second cursor determined by the difference, once the third feature point is selected.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Embodiments of an ultrasonic apparatus and method for controlling the same will now be described in detail with reference to accompanying drawings.

Figure 1:
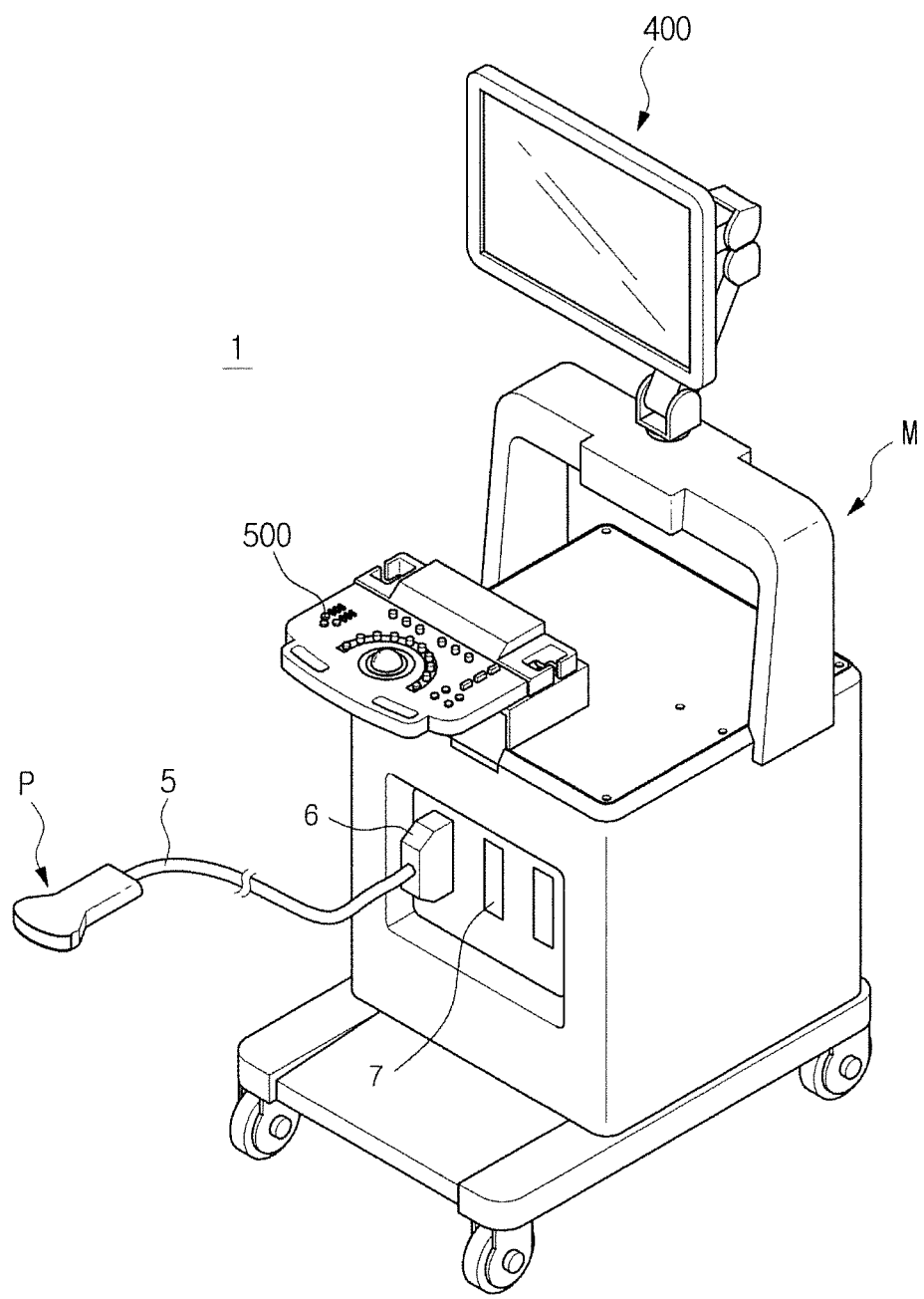
FIG. 1 is a perspective view of an ultrasonic apparatus, according to an embodiment of the present disclosure.
Figure 2:
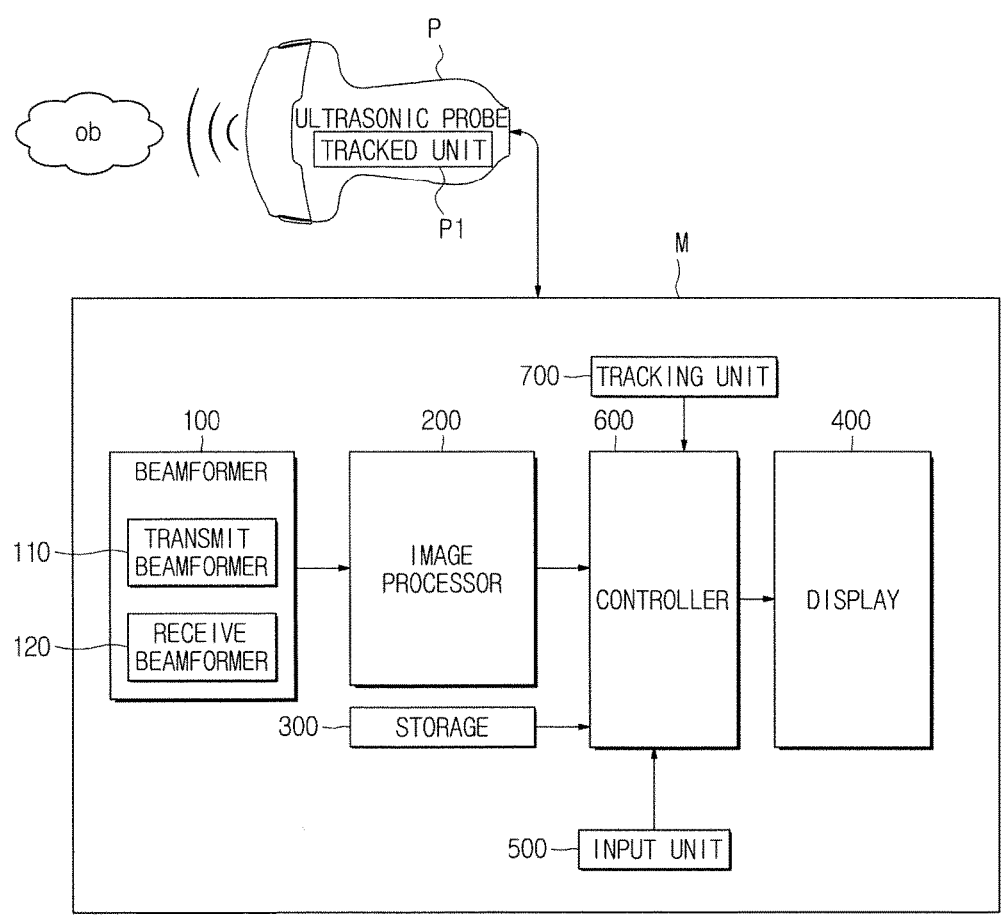
FIG. 2 is a control block diagram of an ultrasonic apparatus, according to an embodiment of the present disclosure.
Figure 3:
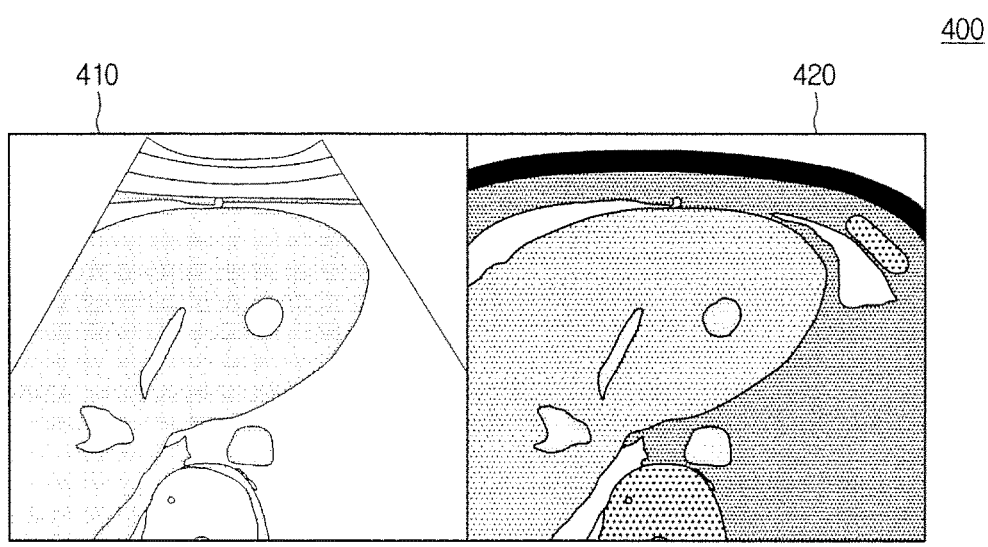
FIG. 3 shows registered ultrasound image and external image displayed on a display, according to an embodiment of the present disclosure.

FIG. 1 is a perspective view of an ultrasonic apparatus, according to an embodiment of the present disclosure, FIG. 2 is a control block diagram of an ultrasonic apparatus, according to an embodiment of the present disclosure, and FIG. 3 shows registered ultrasound image and external image displayed on a display, according to an embodiment of the present disclosure.

Referring to FIG. 1, an ultrasonic apparatus 1 may include a main unit M, and an ultrasonic probe P.

The ultrasonic probe P is a unit that comes in direct contact with the surface of an object to collect echo ultrasounds containing information of the object. For this, the ultrasonic probe P may include a plurality of transducer elements for converting between electric signals and ultrasounds.

The plurality of transducer elements may be arrayed on one side of the ultrasonic probe P. If the transducer elements are arrayed on one side of the ultrasonic probe P in one dimension (1D), the ultrasonic probe P is called a 1D array probe. The 1D array probe may include a linear array prove having transducer elements arrayed in a straight line, a phased array probe, and a convex array probe having transducer elements arrayed in a curve.

Alternatively, if the transducer elements of the ultrasonic probe P are arrayed in two dimensions (2D), the ultrasonic probe P is called 2D array probe. In the 2D array probe, the transducer elements may be arrayed on a plane. For example, the transducer elements may be arrayed to form a curved plane on one side of the 2D array probe.

The transducer elements may generate ultrasounds by vibrating according to transmit signals provided from the main unit M. The ultrasounds may be irradiated to the inside of an object. Furthermore, the transducer elements may vibrate according to echo ultrasounds reflected from a particular region inside the object and generate a receive signal corresponding to the echo ultrasound. The receive signal may be sent to the main unit M to be used to generate an ultrasound image.

Hereinafter, the transmit signal received by the ultrasonic probe P will be called an ultrasound signal, and the receive signal generated by the ultrasonic probe P will be called an echo ultrasound signal.

The ultrasonic probe P may collect echo ultrasounds in real time, and generate echo ultrasound signals with a predetermined time gap. The echo ultrasound signal generated with the time gap may be the basis of a frame image of the ultrasound image.

The ultrasonic probe P may be configured to communicate with the main unit M via a cable 5. For this, the ultrasonic probe P may be connected to an end of the cable 5, the other end of which may be connected to a male connector 6. The mail connector 6 connected to the other end of the cable 5 may be physically connected with a female connector 7 of the main unit M, and as a result, the ultrasonic probe P may be connected to the main unit M.

The ultrasonic probe P may receive the ultrasound signal from the main unit M or transmit the echo ultrasound signal to the main unit M via the cable 5. In addition, the ultrasonic probe P may be controlled by the main unit M by receiving control signals from the main unit M via the cable 5.

Specifically, once a control signal corresponding to a control command input through an input unit 500 is generated by the main unit M, the ultrasonic probe P may be controlled according to the control command by receiving the control signal via the cable 5. For example, once a control command to set a focal depth of an irradiated ultrasound, aperture or shape of the ultrasonic probe P, or a steering angle is input through the input unit 500, the main unit M may generate a control signal corresponding to the control command. The control signal may be sent to the ultrasonic probe P via the cable 5 and used for beamforming.

Alternatively, wireless connection may be used between the main unit M and the ultrasonic probe P200. In this case, the ultrasonic probe P may wirelessly receive an ultrasound signal for ultrasound irradiation, or may wirelessly transmit an echo ultrasound signal corresponding to an echo ultrasound received from an object (ob).

The ultrasonic probe P may be connected to the main unit M by employing any one of wireless communication schemes known to the public. For example, the ultrasonic probe P may be connected to the main unit M in a wireless Internet scheme, such as Wireless Local Area Network (WLAN), Wireless Fidelity (Wi-Fi), Wireless Broadband (Wibro), World Interoperability for Microwave Access (Wimax), High Speed Downlink Packet Access (HSDPA), or in a short range communication scheme, such as Bluetooth, Radio Frequency Identification (RFID), Infrared Data Association (IrDA), Ultra Wideband (UWB), ZigBee, etc.

Positions of the ultrasonic probe P may be tracked by a controller 600, which will be described later. For this, the ultrasonic probe P may further include a tracked unit P1, which may be tracked by electromagnetic waves or beams produced by a tracking unit 700 of the main unit M. Alternatively, the tracked unit P1 may be implemented with an acceleration sensor or a gravity sensor for sending detection results to the tracking unit 700.

Referring to FIG. 2, the main unit M may include a beamformer 100, an image processor 200, a storage 300, a controller 600, an input unit 500, a display 400, and a tracking unit 700.

The tracking unit 700 may track the ultrasonic probe P to obtain information about a position and orientation of the ultrasonic probe P. In an embodiment of the present disclosure, the tracking unit 700 may generate electromagnetic waves and track the tracked unit P1 that is responsive to the electromagnetic waves, to obtain information about a position and orientation of the ultrasonic probe P. In addition, the tracking unit 700 may employ an optical scheme to irradiate beams, e.g., laser beams. If the tracked unit P1 may be implemented with an acceleration sensor or a gravity sensor, the tracking unit 700 may use the detection result from the tracked unit P1 to obtain information about a position and orientation of the ultrasonic probe P.

The information about the position and orientation of the ultrasonic probe P obtained by the tracking unit 700 may be sent to the controller 600.

The beamformer 100 may beamform ultrasound signals for the ultrasonic probe P to irradiate ultrasounds, or beamform echo ultrasound signals received from the ultrasonic probe P. Here, beamforming refers to a scheme to delay and arrange ultrasounds irradiated to a particular point in the object ob or echo ultrasounds reflected from the particular point. This is to compensate for time differences in ultrasounds arriving at the particular point of the object ob or in echo ultrasounds reflected from the particular point arriving at the plurality of transducer elements.

The beamformer 100 may include a transmit beamformer 110 for beamforming ultrasounds irradiated to the object ob, and a receive beamformer 120 for beamforming collected echo ultrasounds.

The beamformer 100 may employ any beamforming scheme known to the public, or may apply one or a combination of a plurality of beamforming schemes.

The echo ultrasound signal beamformed by the beamformer 100 is sent to the image processor 200 to be used in creating an ultrasound image.

The image processor 200 may process the echo ultrasound signal beamformed by the beamformer 100 to create an ultrasound image, and send the ultrasound image to the display 400 to provide the user with anatomical information of the object. For this, the image processor 200 may be implemented in hardware, such as a microprocessor, or in software that may be carried out in the hardware.

The storage 300 may store an external image of the object ob in advance, which has been acquired by an external imaging apparatus. Especially, the storage 300 may store a volume image of the object ob in advance, which includes volume information of the object ob.

For example, the storage 300 may store a Computerized Tomography (CT) image of the object ob acquired by an external CT scanner or a Magnetic Resonance (MR) image of the object ob acquired by an external Magnetic Resonance Imaging (MRI) device in advance.

Furthermore, the storage 300 may store various information required to control the ultrasonic apparatus 1. For example, the storage 300 may store registration parameters used in registration between an ultrasound image and an external image.

For this, the storage unit 300 may be implemented with at least one type of storage media, such as flash memories, hard disks, multimedia card micro type memories, card type memories (e.g., SD or XD memories), Random Access Memories (RAMs), Static Random Access Memories (SRAMs), Read-Only Memories (ROMs), Electrically Erasable Programmable Read-Only Memories (EEPROMs), Programmable Read-Only Memories (PROMs), magnetic memories, magnetic disks, and optical disks.

Although the storage 300 of FIG. 2 is equipped in the main unit M, the storage 300 may be linked to the main unit M through an external interface of the main unit M in another embodiment. Alternatively, the storage 300 may be implemented in e.g., an external server that makes up a network common to the ultrasonic apparatus 1.

The display 400 may display an ultrasound image created by the image processor 200. The user may visually perceive anatomical information of the object ob from the ultrasound image displayed through the display 400.

Furthermore, the display 400 may display an external image stored in advance in the storage 300. Especially, if the external image includes a volume image of the object ob, the display 400 may display one of cross-sectional images of the object ob that make up the volume image.

In addition, the display 400 may display an ultrasound image and an external image at the same time. For example, the display 400 may display registered ultrasound image and external image.

Although the single display 400 is arranged in FIG. 1, the display 400 may be implemented in the multiple number of displays in another embodiment. In this case, one of the multiple displays 400 displays an ultrasound image while another of them displays an external image.

The input unit 500 is arranged in the main unit M for receiving commands related to operation of the ultrasonic apparatus 1. For example, the input unit 500 may receive a command to start ultrasound diagnosis or a command to make a mode selection for an ultrasound image.

Furthermore, the input unit 500 may receive a command to select a feature point for registration between an ultrasound image and an external image. This will be described in more detail later.

The input unit 500 may include various means for the user to input control commands, such as a keyboard, a mouse, a trackball, a tablet, a touch screen module, etc.

The controller 600 may control the respective components of the ultrasonic apparatus 1 according to a control command of the user input through the input unit 500 or according to the internal operation.

Furthermore, the controller 600 may register an ultrasound image created by the image processor 200 and an external image stored in advance in the storage 300, and control the display 400 to display the registered two images.

To register the ultrasound image and external image, the controller 600 may first acquire a transformation matrix for registration. Specifically, the controller 600 may acquire a rotation transformation matrix for rotation transformation of a coordinate axis and a position transformation matrix for moving the position of a coordinate axis. How to acquire the rotation transformation matrix will be described first, and how to acquire the position transformation matrix will be followed.

To acquire a rotation transformation matrix, the controller 600 may set a reference coordinate system and transform a coordinate system applied to an ultrasound image to the reference coordinate system. The reference coordinate system as herein used may refer to a coordinate system having the origin set to be a position of the tracking unit 700 that produces electromagnetic waves to track the tracked unit P1 of the ultrasonic probe P.

Subsequently, the input unit 500 may receive a control command from the user to select a cross-sectional image of the object ob at a particular position from among external images. The user may check an ultrasound image being displayed on the display 400 and then select a cross-sectional image of the object ob at the same position as that of the ultrasound image from among cross-sectional images that make up a volume image of the object ob.

The controller 600 may then transform a coordinate system applied to the selected cross-sectional image of the object ob to a coordinate system of the whole volume image. The coordinate system of the volume image may have coronal, Sagittal, and axial planes.

Finally, the controller 600 may acquire a rotation transformation matrix to transform the reference coordinate system to the coordinate system of the volume image. For this, the controller 600 may calculate an extent of deviation, i.e., a rotation angle of the coordinate system of the volume image with respect to the reference coordinate system.

After the rotation transformation matrix is acquired, the input unit 500 may receive a command from the user to select a feature point, which refers to an anatomically identical position on the ultrasound image and the cross-sectional image. For example, the user may select a feature point on the ultrasound image, and then select a feature point on the external image at the anatomically identical position as the feature point on the ultrasound image. Alternatively, the user may select a feature point on the external image, and then select a feature point on the ultrasound image at the anatomically identical position as the feature point on the external image.

In the following description, for convenience of explanation, it is assumed that a feature point of an ultrasound image is selected first and a feature point of an external image is selected next.

Once the feature points are selected, the controller 600 may transform coordinates of the feature point on the ultrasound image into the reference coordinate system. Since the position and orientation information of the ultrasonic probe P may be obtained by the tracking unit 700, the controller 600 may use the information to obtain the coordinates of the feature point of the ultrasound image in the reference coordinate system.

Also, the controller 600 may transform coordinates of the feature point on an external image into the coordinate system of the volume image.

Lastly, the controller 600 may acquire a translation transformation matrix to transform the reference coordinate system to the coordinate system of the volume image. For this, the controller 600 may calculate a difference in coordinates of a feature point between the ultrasound image in the reference coordinate system and the external image in the coordinate system of the volume image.

After acquiring the transformation matrix through the above procedure, the controller 600 may register the external image with the displayed ultrasound image in real time. Furthermore, the controller 600 may control the display 400 to display the registered ultrasound image and external image together.

Referring to FIG. 3, the display 400 may display the ultrasound image in a predetermined first area 410 and the external image registered with the ultrasound image in a predetermined second area 420.

In the meantime, the user may perform ultrasonic diagnosis while moving the ultrasonic probe P. Accordingly, the display 400 may display an ultrasound image at a position of the object ob according to the movement of the ultrasonic probe P, and simultaneously display an external image registered with the ultrasound image in real time.

At this time, there may be a registration error between the ultrasound image and the external image. The registration method as described above is performed based on the assumption of image registration for a rigid body, but the human body is actually a non-rigid body, so the registration might become less accurate.

For example, if the coordinate system is changed due to a movement of the object ob, such as breathing, registration is performed on an object image in which a plurality of feature points are set, or there exists an error in selecting a feature point on a volume image, the registration may be inaccurately performed.

Especially, in a case the object ob is a large organ, such as the liver, it is difficult to acquire an ultrasound image for the whole object ob through one time ultrasound scanning, and thus an anatomical position error might occur in selecting a feature point, which may cause a registration error.

In such a case, initial registration is performed on an organ allowing the user to relatively accurately select a feature point therein, such as a vein, and then re-registration may be performed by selecting a feature point for the object located in close proximity to the organ. In the re-registration, the rotation transformation matrix for the rotation angle may remains the same, while the translation transformation matrix acquired based on a difference in feature point coordinates between the two images may be re-calculated.

Figure 4:
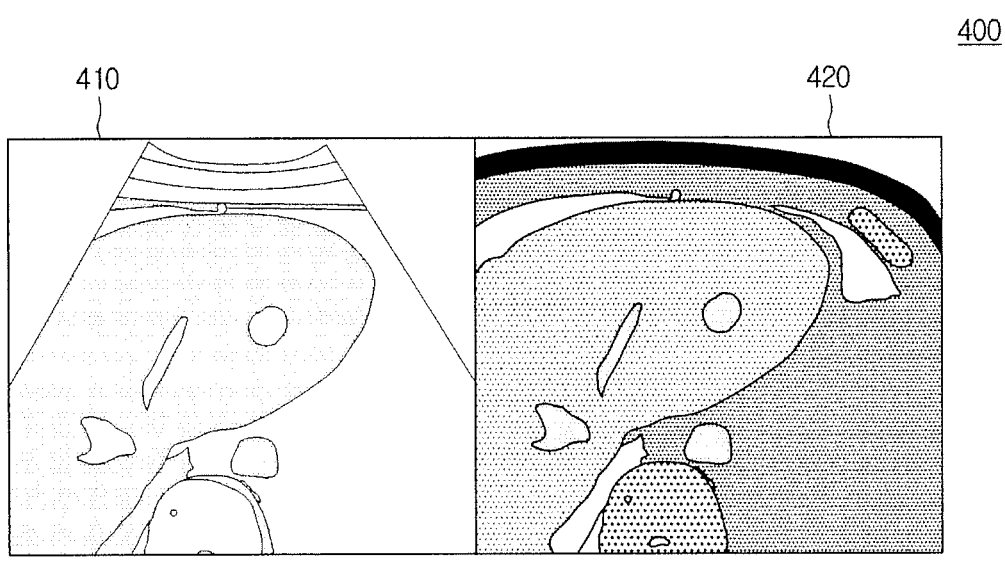
FIG. 4 shows registered ultrasound image and external image with a registration error, which is displayed on a display, according to an embodiment of the present disclosure.
Figure 5A:
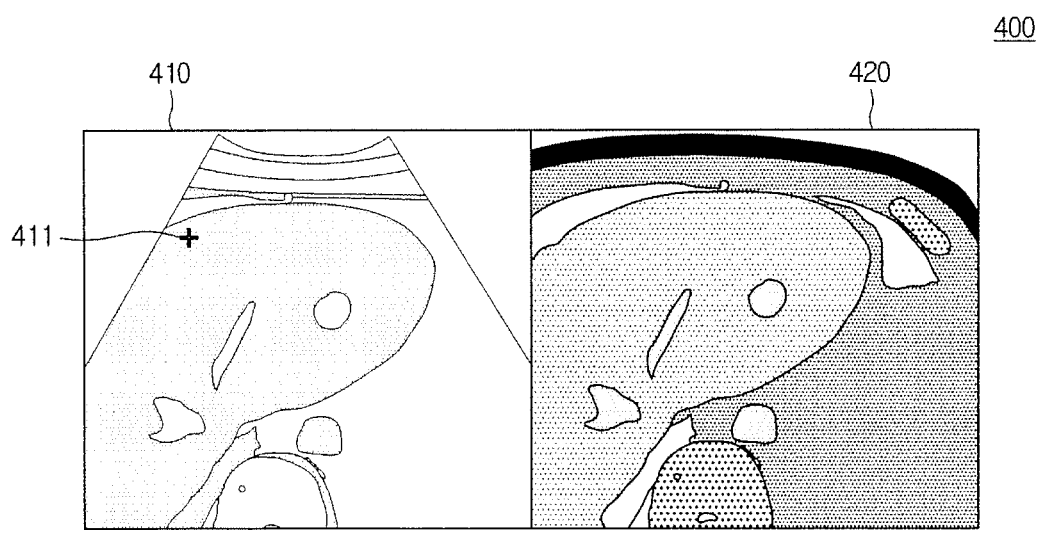
FIGS. 5A to 5C show a cursor for re-registration displayed on a display, according to an embodiment of the present disclosure.
Figure 5B:
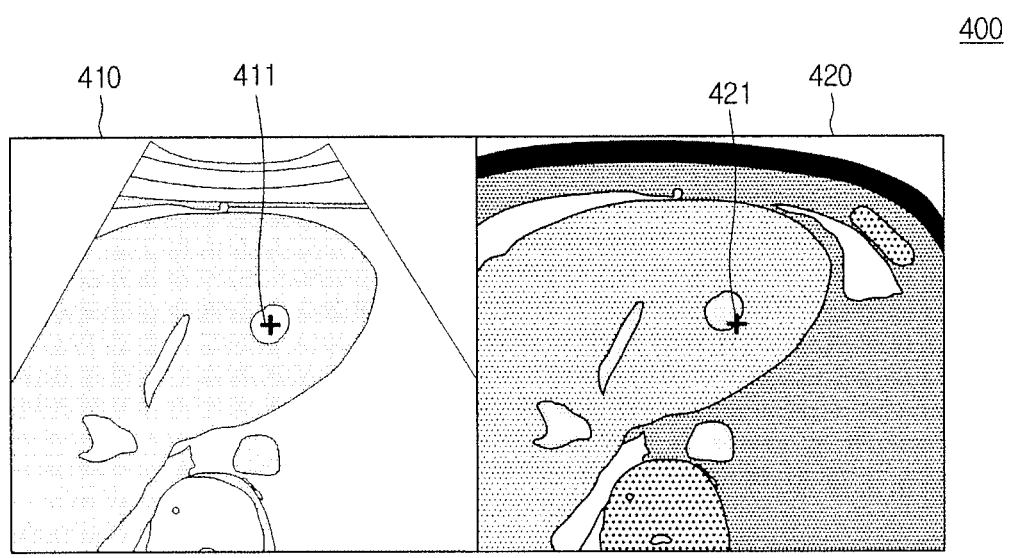
Figure 5C:
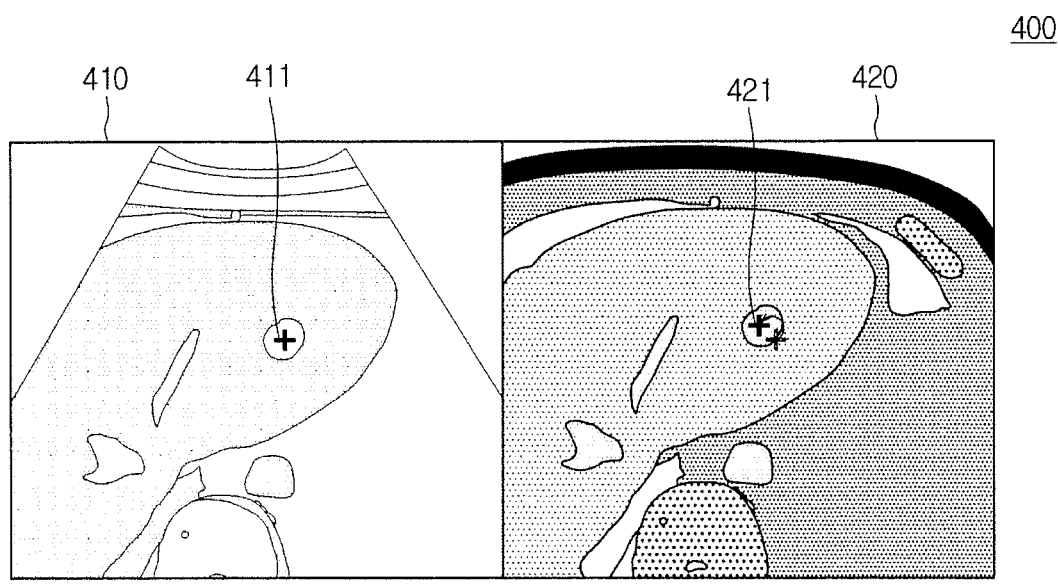

FIG. 4 shows registered ultrasound image and external image with a registration error, which is displayed on a display, according to an embodiment of the present disclosure, and FIGS. 5A to 5C show a cursor for re-registration displayed on a display, according to an embodiment of the present disclosure.

As described above, FIG. 3 shows registration between an ultrasound image and an external image without an error. In contrast, it is seen from FIG. 4 that there exists an error between an anatomical position in which an ultrasound image appears and an anatomical position in which an external image appears.

In this case, the input unit 500 may receive a re-registration command from the user. Upon reception of the re-registration command, the controller 600 may control the display 400 to display a cursor for feature point re-selection.

Referring to FIG. 5A, the display 400 may display a first cursor 411 for feature point re-selection on the ultrasound image. The input unit 500 may receive a cursor movement command, and the controller 600 may control the display 400 to move the first cursor 411 in response to the cursor movement command.

Referring to FIG. 5B, when the first cursor 411 reaches a point to be reselected as a feature point, the input unit 500 may receive a feature point re-selection command for the ultrasound image. The controller 600 may then reselect the point of the first cursor 411 as a feature point on the ultrasound image while controlling the display 400 to display the first cursor 411 in a different color. For example, the display 400 may display the first cursor 411 in green while the first cursor 411 is in the movement mode, and upon reception of the feature point re-selection command, display the first cursor 411 in red.

Furthermore, after the feature point re-selection command is received for the ultrasound image, the controller 600 may control the display 400 to display a second cursor 421 for feature point re-selection on the external image.

In this regard, the controller 600 may use the transformation matrix that has been used in previous registration of the two images to determine where to place the second cursor 421 on the external image. Specifically, the controller 600 may obtain corresponding coordinates on the external image by applying the transformation matrix to the coordinates of the feature point on the ultrasound image. The controller 600 may display the second cursor 421 on the obtained coordinates.

If re-registration is performed following the previous image registration, there may not typically be significant registration error. Accordingly, once a point for the second cursor 421 to be displayed on the external image is determined by using the transformation matrix that has been used in the previous image registration, it is more likely to have a point to be reselected as a feature point in close proximity to the point where the second cursor 421 is displayed. As a result, the user may easily reselect the feature point, thereby reducing time spent on registration.

After the second cursor 4210 is displayed on the external image, the input unit 500 may receive a cursor movement command, and the controller 600 may control the display 400 to move the second cursor 421 in response to the cursor movement command.

Lastly, referring to FIG. 5C, when the second cursor 421 reaches a point to be reselected as a feature point, the input unit 500 may receive a feature point re-selection command for the external image. The controller 600 may then reselect the point of the second cursor 421 as a feature point on the external image while controlling the display 400 to display the second cursor 421 in a different color. For example, the display 400 may display the second cursor 421 in green while the second cursor 421 is in the movement mode, and upon reception of the feature point re-selection command, display the second cursor 421 in red.

Once the feature points are reselected on the ultrasound image and external image, the controller 600 may reset the transformation matrix using coordinates of the selected feature points.

In addition to the aforementioned method, other various methods may be used to display various screens on the display 400 for re-selection of feature points.

Figure 6A:
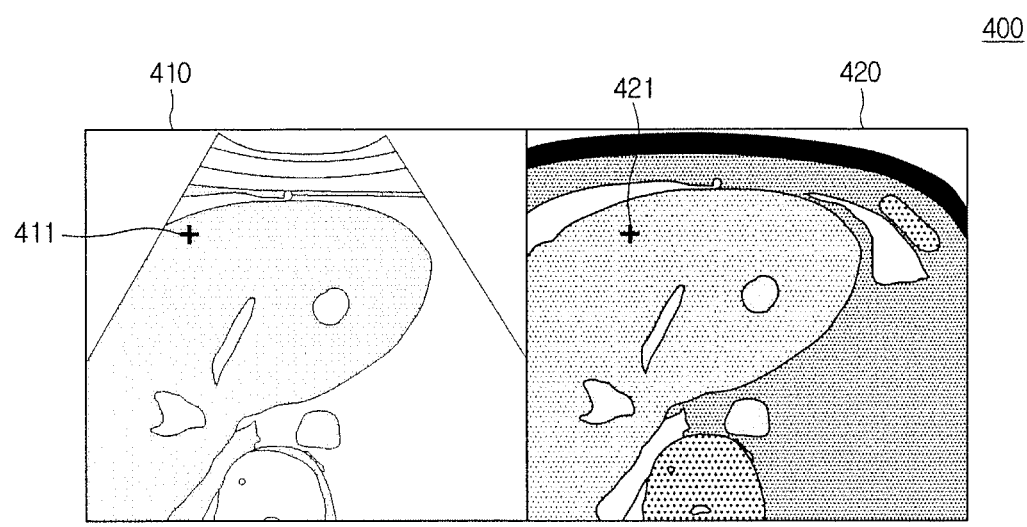
FIGS. 6A to 6C show a cursor for re-registration displayed on a display, according to another embodiment of the present disclosure.
Figure 6B:
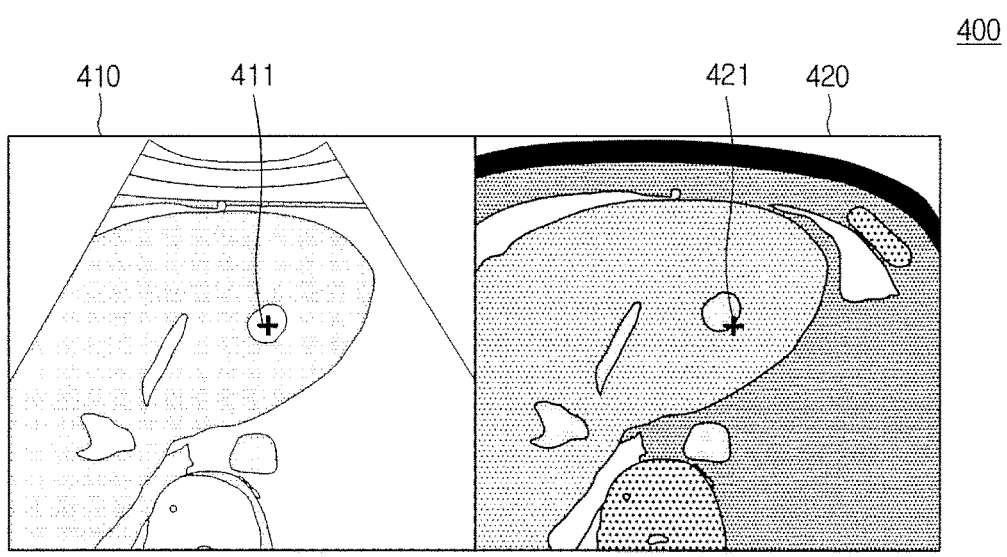
Figure 6C:
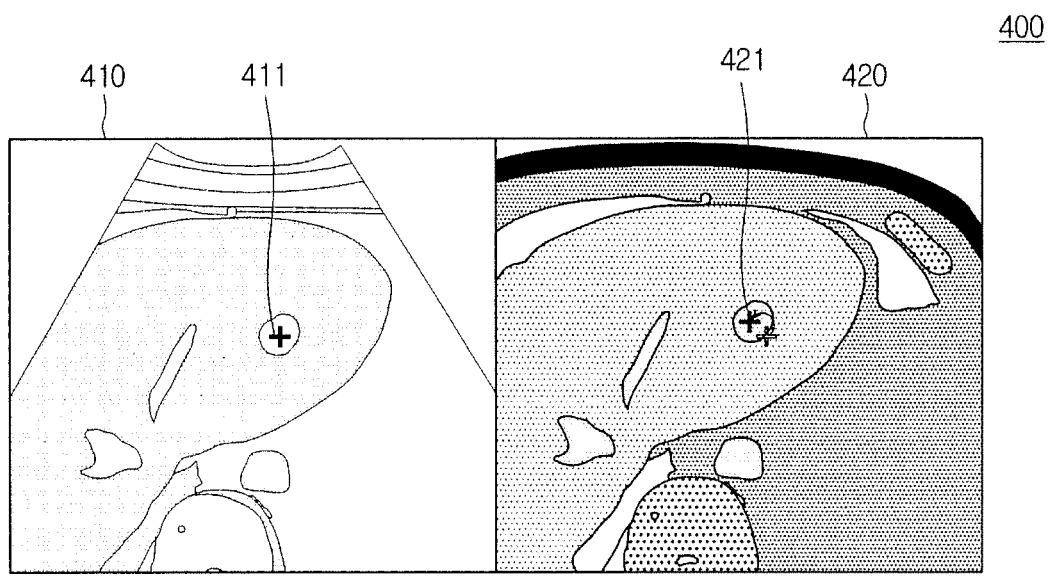

FIGS. 6A to 6C show a cursor for re-registration displayed on a display, according to another embodiment of the present disclosure.

The input unit 500 may receive a re-registration command from the user. Upon reception of the re-registration command, the controller 600 may control the display 400 to display a cursor for feature point re-selection.

Referring to FIG. 6A, the display 400 may display cursors 411, 421 for re-selection of feature points on the ultrasound image and the external image. The input unit 500 may receive a cursor movement command, and the controller 600 may control the display 400 to move the cursor 411 or 421 in response to the cursor movement command.

In this regard, the controller 600 may use the transformation matrix that has been used in previous registration of the two images to determine where to place the second cursor 421 on the external image. Specifically, the controller 600 may obtain corresponding coordinates on the external image by applying the transformation matrix to the coordinates of the feature point on the ultrasound image. The controller 600 may display the second cursor 421 on the obtained coordinates.

In this case, a registration error of the two images may be visually determined by comparing a difference between the first cursor 411 and second cursor 421 moving on the ultrasound image and external image, respectively.

Referring to FIG. 6B, when the first cursor 411 reaches a point to be reselected as a feature point, the input unit 500 may receive a feature point re-selection command for the ultrasound image. The controller 600 may then reselect the point of the first cursor 411 as a feature point on the ultrasound image while controlling the display 400 to display the first cursor 411 in a different color. For example, the display 400 may display the first cursor 411 in green while the first cursor 411 is in the movement mode, and upon reception of the feature point re-selection command, display the first cursor 411 in red.

Subsequently, the input unit 500 may receive a cursor movement command for the external image. In response to the cursor movement command, the controller 600 may control the display 400 to move the displayed second cursor 421

Lastly, referring to FIG. 6C, when the second cursor 421 reaches a point to be reselected as a feature point, the input unit 500 may receive a feature point re-selection command for the external image. The controller 600 may then reselect the point of the second cursor 421 as a feature point on the external image while controlling the display 400 to display the second cursor 421 in a different color. For example, the display 400 may display the second cursor 421 in green while the second cursor 421 is in the movement mode, and upon reception of the feature point re-selection command, display the second cursor 421 in red.

Once the feature points are reselected on the ultrasound image and external image, the controller 600 may reset the transformation matrix using coordinates of the selected feature points.

Figure 7A:
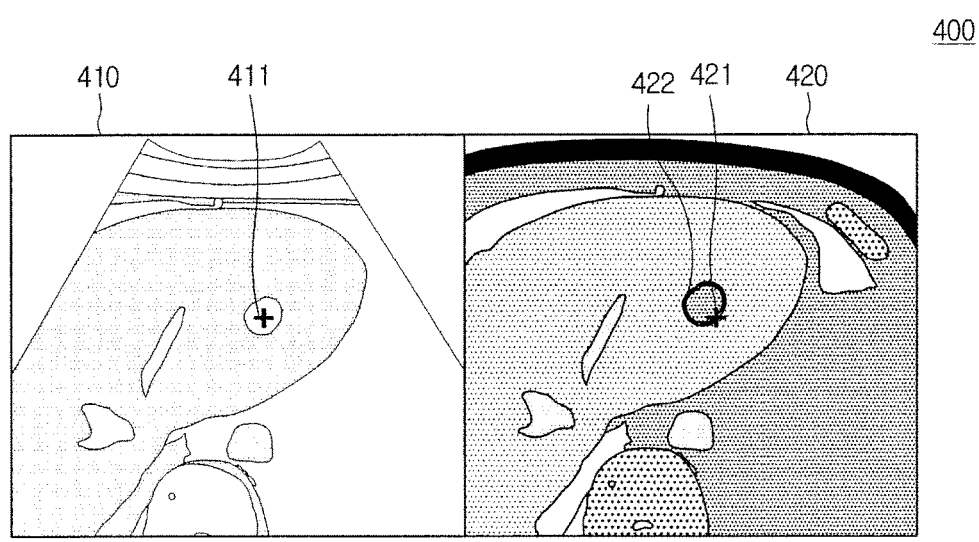
FIGS. 7A and 7B show a cursor for re-registration displayed on a display, according to another embodiment of the present disclosure.
Figure 7B:
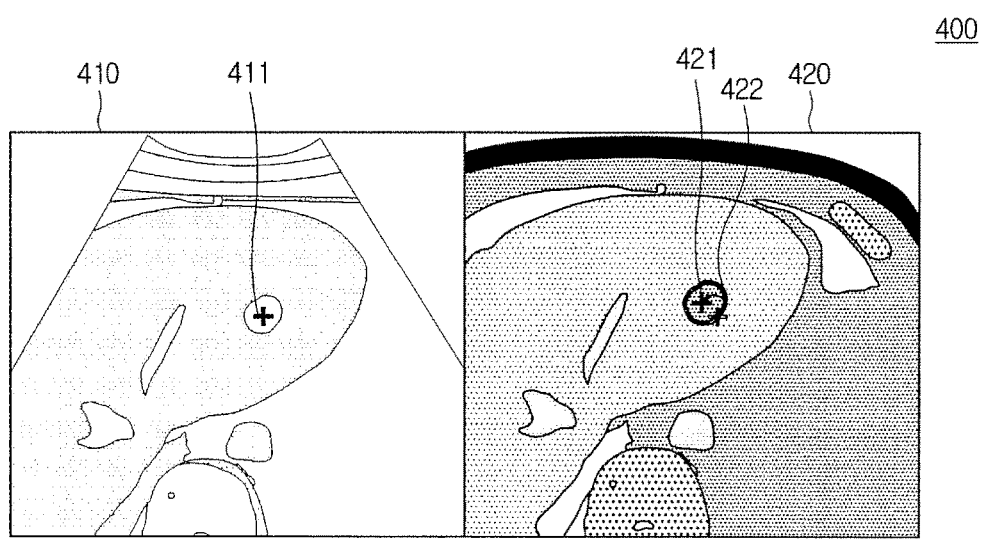

FIGS. 7A and 7B show a cursor for re-registration displayed on a display, according to another embodiment of the present disclosure.

Referring to FIG. 7A, when the first cursor 411 reaches a point to be reselected as a feature point on the ultrasound image, the input unit 500 may receive a feature point re-selection command for the ultrasound image. In response to the command, the controller 600 may reselect a point of the first cursor 411 as a feature point on the ultrasound image while controlling the display 400 to display the first cursor 411 in a different color.

Furthermore, after the feature point re-selection command is received for the ultrasound image, the controller 600 may control the display 400 to display a second cursor 421 for feature point re-selection on the external image.

In this regard, the controller 600 may use the transformation matrix that has been used in previous registration of the two images to determine where to place the second cursor 421 on the external image. Specifically, the controller 600 may obtain corresponding coordinates on the external image by applying the transformation matrix to the feature coordinates on the ultrasound image. The controller 600 may display the second cursor 421 on the obtained coordinates.

Furthermore, the controller 600 may set the point of the second cursor 421 on the external image as a seed point to control the image processor 200 to perform segmentation. With the segmentation, the image processor 200 may extract an area including the point of the second cursor 421 on the external image.

Once the area including the point of the second cursor 421 is extracted, the controller 600 may control the display 400 to display the area with some emphasis. Since a feature point to be reselected may exist in close proximity to the point of the second cursor 421, it is more likely for the feature point to be include in the area having the point of the second cursor 421. Accordingly, the user may easily reselect the feature point by displaying with emphasis on the area including the point of the second cursor 421.

Lastly, referring to FIG. 7B, when the second cursor 421 reaches a point to be reselected as a feature point, the input unit 500 may receive a feature point re-selection command for the external image. As in the previous embodiments, in response to the command, the controller 600 may reselect the point of the second cursor 421 as a feature point on the external image while controlling the display 400 to display the second cursor 421 in a different color.

Once the feature points are reselected on the ultrasound image and external image, the controller 600 may reset the transformation matrix using coordinates of the selected feature points.

In re-registration, there may be various embodiments of a user input method. For example, the re-registration command or the feature point re-selection command may be input by pressing a corresponding key or button in the input unit 500. In another example, the re-registration command or the feature point re-selection command may be input by clicking a corresponding icon in a user interface (UI) displayed on the display 400.

In still another example, the re-registration command or the feature point re-selection command may be input by pressing or releasing a predetermined key or button. For example, when the predetermined key is pressed, re-registration is started and the display 400 may display the first cursor 411 on the ultrasound image. While the predetermined key remains pressed, the input unit 500 may receive a cursor movement command. When the pressure on the predetermined key is released, the input unit 500 may receive a command to reselect the point of the first cursor 411 at that moment as a feature point.

Figure 8:
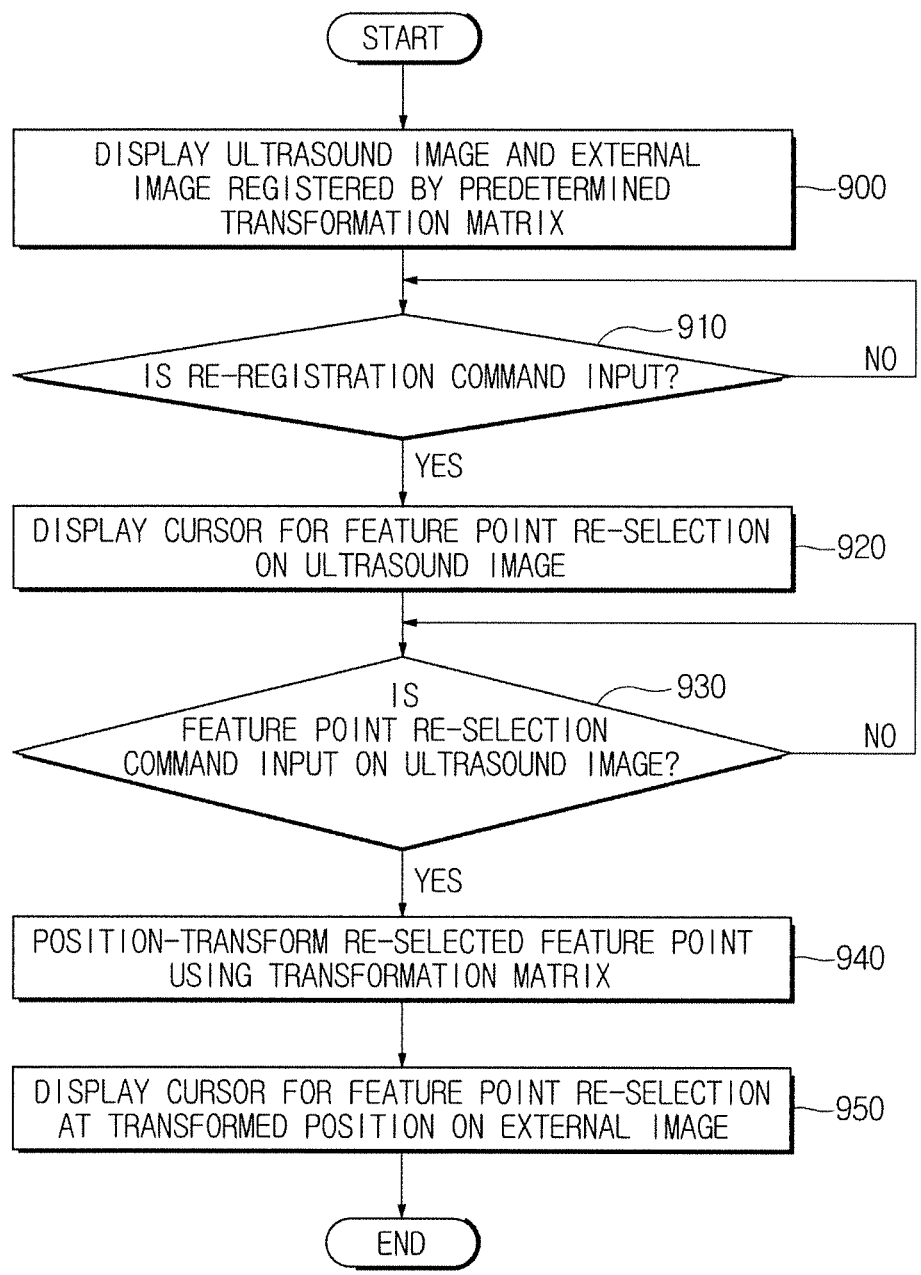
FIG. 8 is a flowchart illustrating a method for controlling an ultrasonic apparatus, according to an embodiment of the present disclosure.

FIG. 8 is a flowchart illustrating a method for controlling an ultrasonic apparatus, according to an embodiment of the present disclosure.

First, the ultrasonic apparatus 1 may display an ultrasound image and an external image, which are registered by a predetermined transformation matrix, in operation 900. Specifically, the controller 600 of the ultrasound apparatus 1 may acquire a transformation matrix for registration, and register the ultrasound image and the external image using the transformation matrix. Next, the display 400 of the ultrasonic apparatus 1 may simultaneously display the registered ultrasound image and external image at the same time.

The ultrasonic apparatus 1 may determine whether a re-registration command has been input, in operation 910. If no re-registration command has been input, the ultrasonic apparatus 1 may repeatedly determine whether a re-registration command has been input.

Otherwise, if a re-registration command has been input, the ultrasonic apparatus 1 may display a cursor for re-selection of a feature point on the ultrasound image, in operation 920. The ultrasonic apparatus I may receive a cursor movement command, and move the cursor to a point corresponding to the command.

The ultrasonic apparatus 1 may determine whether a feature point re-selection command for the ultrasound image has been received, in operation 930. If the feature point re-selection command has not been input, the ultrasonic apparatus 1 may repeatedly determine whether the feature point re-selection command has been input.

Otherwise, if the feature point re-selection command has been input, the ultrasonic apparatus 1 may perform position transformation on the reselected feature point on the ultrasound image using a transformation matrix, in operation 940. The transformed position may refer to a position in the coordinate system applied to the external image.

Lastly, the ultrasonic apparatus I may display a cursor for feature point re-selection at the transformed position on the external image, in operation 950. Since an error in registration between the ultrasound image and the external image is not significant, it is more likely that a feature point to be reselected exists in close proximity to a point where the cursor is displayed. Accordingly, the user may easily select the feature point, thereby reducing time spent on re-registration.

It has thus far been described that in registration and re-registration between an ultrasound image and an external image, a feature point on the ultrasound image is first selected and then a cursor is displayed on the external image at a point corresponding to the selected feature point. However, in some other embodiments, it is also possible to select a feature point on the external image first and then display a cursor on the ultrasound image at a position corresponding to the selected feature point. In addition, in other embodiments, a feature point for one of the ultrasound image and the external image may be automatically selected by internal computation of the ultrasonic apparatus I, and then a cursor may be displayed on the other one of the ultrasound image and the external image at a point corresponding to the selected feature point.

According to embodiments of the present disclosure, a distance between a cursor and a feature point may be short by displaying the cursor on a point determined based on a registration parameter that was used in previous registration.

As a result, the user may select the feature point more quickly, thereby reducing time spent on re-registration of an ultrasound image and an external image.

DESCRIPTION OF THE SYMBOLS

1: ULTRASONIC APPARATUS
P: ULTRASONIC PROBE
M: MAIN UNIT
200: IMAGE PROCESSOR
300: STORAGE
400: DISPLAY
500: INPUT UNIT
600: CONTROLLER

What is claimed is:

1. An ultrasonic apparatus comprising:
a controller configured to use a difference in coordinates between a first feature point of an ultrasound image and a second feature point of an external image with respect to a reference coordinate system, to register the ultrasound image and the external image; and
a display configured to display the registered ultrasound image and external image;
an input device configured to receive a command to select third and fourth feature points for re-registration,
wherein the controller is further configured to:
control the display to display at least one of a first cursor for selection of the third feature point or a second cursor for selection of the fourth feature point;
once the third feature point of one of the ultrasound image and the external image is selected, control the display to display the second cursor for selection of the fourth feature point at a position corresponding to the third feature point on the other one of the ultrasound image and the external image based on the difference in coordinates between the first feature point and the second feature point; and
control the display to display a third cursor on a position adjacent to the second cursor, and the position of the third cursor is based on the difference in coordinates between the first feature point and the second feature point.

2. The ultrasonic apparatus of claim 1, wherein the controller is configured to, while the first and second cursors are displayed at the same time, if the first cursor is moved to select the third feature point, control the display to display the second cursor at a position corresponding to the moved position of the first cursor based on the difference in coordinates between the first feature point and the second feature point.

3. The ultrasonic apparatus of claim 1, wherein the controller is configured to control the display to display the first cursor in a changed color, once the third feature point is selected.

4. The ultrasonic apparatus of claim 1, wherein the controller is configured to control the display to display an area with emphasis, the area including the position of the second cursor determined based on the difference in coordinates between the first feature point and the second feature point, once the third feature point is selected.

5. A method for controlling an ultrasonic apparatus, the method comprising:
- using a difference in coordinates between a first feature point of an ultrasound image and a second feature point of an external image with respect to a reference coordinate system, to register the ultrasound image and the external image;
- displaying the registered ultrasound image and external image;
- receiving a re-registration command for selecting third and fourth feature points;
- displaying at least one of a first cursor for selection of the third feature point or a second cursor for selection of the fourth feature point;
- once the third feature point of one of the ultrasound image and the external image is selected for re-registration, displaying the second cursor for selection of the fourth feature point at a position corresponding to the third feature point on the other one of the ultrasound image and the external image based on the difference in coordinates between the first feature point and the second feature point; and
- displaying a third cursor on a position adjacent to the second cursor, and the position of the third cursor is based on the difference in coordinates between the first feature point and the second feature point.

6. The method of claim 5, wherein displaying a cursor for selection of a fourth feature point comprises:
- displaying the first cursor;
- receiving a command to select the position of the first cursor to be the third feature point; and
- displaying the second cursor at a position corresponding to the third feature point based on the difference in coordinates between the first feature point and the second feature point.

7. The method of claim 6, further comprising:
- once the first cursor is moved to select the third feature point, displaying the second cursor on a position corresponding to a moved position of the first cursor based on the difference in coordinates between the first feature point and the second feature point.

8. The method of claim 6, further comprising:
- displaying the first cursor in a changed color, once the third feature point is selected.

9. The method of claim 6, further comprising:
- displaying an area with emphasis, the area including the position of the second cursor determined based on the difference in coordinates between the first feature point and the second feature point, once the third feature point is selected.

* * * * *